United States Patent [19]

Finot et al.

[11] 4,052,372

[45] Oct. 4, 1977

[54] PREPARATION OF ε-(γ-GLUTAMYL)-LYSINE

[75] Inventors: Paul-Andre Finot, Vevey; Pierre Hirsbrunner, Corseaux; Raymond Bertholet, Aigle, all of Switzerland

[73] Assignee: Societe d'Assistance Technique pour Produits Nestle S.A., Lausanne, Switzerland

[21] Appl. No.: 653,704

[22] Filed: Jan. 30, 1976

[30] Foreign Application Priority Data

Feb. 7, 1975 Switzerland .......................... 1536/75

[51] Int. Cl.$^2$ ............................................. C07C 103/52
[52] U.S. Cl. ............................................... 260/112.5 R
[58] Field of Search ................................. 260/112.5 R

[56] References Cited

PUBLICATIONS

Zahn et al., Chem. Abstr. 60:658a (1964).
Kornguth et al., Biochem., 2, 740–745 (1963).

*Primary Examiner*—Delbert R. Phillips
*Attorney, Agent, or Firm*—Watson, Leavenworth, Kelton & Taggart

[57] ABSTRACT

A process for the preparation of ε-(γ-glutamyl)-lysine which comprises heating lysine glutamate for at least 5 hours at a temperature of at least 120° C by means of an inert heat-carrier fluid, and isolating ε-(γ-glutamyl)-lysine from the conversion product thus obtained.

The inert heat-carrier fluid can be either a gas such as air or nitrogen, or a liquid such as n-amylalcohol, kerosene, nonane, 1,1,2,2-tetrachloroethane, 1-octanol or 2-ethyl-1-butanol.

9 Claims, No Drawings

PREPARATION OF ε-(γ-GLUTAMYL)-LYSINE

BACKGROUND OF THE INVENTION

1. Field of the Invention

This invention relates to a process for the preparation of ε-(γ-glutamyl)-lysine from lysine glutamate.

2. Description of the Prior Art

ε-(γ-glutamyl)-lysine (epsilon-(gamma-glutamuyl)-lysine) is one of the possible condensation products of lysine, an essential basic amino acid, and glutamic acid, an acid amino acid. It is not a peptide in the accepted sense of the term, because the lysine is engaged by its amino group in the ε-position and the glutamic acid by its carboxlic group in the γ-position, whereas genuine peptides and proteins consist in principle of amino acids condensed on their amino or carboxylic groups in the α-position.

However, this ε-derivative of lysine is of particular interest as a dietetic additive because it can be used instead of L-lysine or instead of peptides or proteins rich in lysine for enriching foods poor in lysine, such as cereals, as indicated in German Patent Application No. 2,423,089.

The advantage of a practical, inexpensive synthesis will be immediately appreciated. Unfortunately, both on account of the multiplicity of amino and carboxylic acid reaction sites and on account of the tendecy which glutamic acid has to cyclise into pyrrolidone carboxylic acid or pyroglutamic acid, synthesis by direct coupling of the two elemental amino acids is only possible by adopting the conventional methods for the chemical synthesis of peptides, which comprises protecting certain reaction sites whilst activating others, and removing the protective and activating groups on completion of the reaction from the entities present. This leads to a reaction with a multiplicity of stages and only modest yields. In addition, these groups are removed in the present case by hydrogenolysis on palladium so as to avoid rearrangements (cf. for example J. Biol. Chem. 248 (8), 2536, 1973), which results in high production costs.

SUMMARY OF THE INVENTION

By contrast, the present invention enables ε-(γ-glutamyl)-lysine to be produced at moderate cost. The present invention provides a process for the preparation of ε-(γ-glutamyl)-lysine which comprises heating lysine glutamate for at least 5 hours at a temperature of at least 120° C by means of an inert heat-carrier fluid, and isolating ε-(γ-glutamyl)-lysine from the conversion product thus obtained.

DESCRIPTION OF THE PREFERRED EMBODIMENTS

Lysine glutamate is a salt of the alkyl-ammonium carboxylate type, of which the melting point is from 170° to 180° C (with decomposition). According to the invention, it loses one molecule of water by heating with formation of the amide bond of ε-(γ-glutamyl)-lysine. Lysine glutamate may be prepared from a mixture of its two constituent amino acids, for example from an approximately equimolecular mixture of monosodium glutamate and lysine hydrochloride. This mixture is dissolved in water and the lysine glutamate salt is crystallised by adding methanol and seeding with a few crystals of lysine glutamate from a previous production cycle with gentle cooling. This lysine glutamate contains a few percent of sodium chloride. It is purified by dissolution in water, recrystallisation by the addition of methanol and seeding at a temperature around 0° C.

The lysine glutamate crystals thus obtained are crystals of lysine glutamate dihydrate. It has been found that they are in the form of two solid phases, called α and β, which may be distinguished from the X-ray diffraction patterns (according to Debye-Scherrer). The α-phase is stable at 10° C and below, whilst the β-phase is stable above 60° C. The phase obtained by the preparation mentioned above is the α-phase.

In the context of the invention, a heat-carrier fluid is any fluid capable of performing the dual function of transferring to the lysine glutamate calories introduced by heating, and of storing heat. It is possible to use as the heat-carrier fluid a gas, such as air or nitrogen, of which the temperature is carefully regulated (as with an oven for example). It is also possible to use a liquid which must of course be inert with respect to the lysine glutamate, i.e. should not dissolve it, even partially, or react chemically with it. Liquids which satisfy these requirements are for example, nonane, 1,1,2,2-tetrachloroethane, 1-octanol, 2-ethyl-1-butanol, n-amyl alcohol and 1-pentanol. Other fluids of the same kind may be used providing they have boiling points above 120° C which is the temperature required for initiating the conversion of the lysine glutamate.

The various parameters which affect the yields are above all the type of starting lysine glutamate used (α or β phase), the heating temperature and also the heating time. Generally, it has been found that the α-phase gives better yields than the β-phase, that the optimum heating temperature is of the order of 135° to 150° C and that the optimum heating time is from 16 to 48 hours. Heating is preferably carried out in a nitrogen atmosphere or in a stream of nitrogen. Some data are given in the following Table in which the yields quoted are the yields of ε-(γ-glutamyl)-lysine after isolation and purification, and in which AmOH represents n-amyl alcohol.

| Type of lysine glutamate | Heating temperature ° C | Type of heat-carrier fluid | Heating time h | Yields % |
| --- | --- | --- | --- | --- |
| α phase | 130 | AmOH | 16 | 31 |
|  | 130 | kerosene | 16 | 28.5 |
|  | 140 | AmOH | 16 | 45 |
|  | 140 | AmOH | 40 | 48 |
|  | 150 | nonane | 8 | 27.5 |
|  | 150 | nonane | 16 | 45 |
|  | 160 | nonane | 16 | 35 |
| β phase | 135 | AmOH | 16 | 25 |
|  | 140 | AmOH | 16 | 31 |
|  | 150 | nonane | 16 | 28 |

Although these yields may appear low, it is pointed out that the products which have not reacted may be recycled.

The preferred heat-carrier fluid is n-amyl alcohol because its boiling point under atmospheric pressure (138° C) corresponds to the optimum heating temperatures which enables conversion of the lysine glutamate to be carried out very conveniently at the reflux temperature of the n-amyl alcohol. In addition, it forms an azeotrope with water so that it is possible readily to eliminate both the water formed during the conversion and the residual n-amyl alcohol.

The conversion product obtained is a mixture generally containing from 40 to 50% of ε-(γ-glutamyl)-lysine, 25 to 35% of unreacted lysine glutamate, 10 to 15% of lysine and 2 to 5% of unknown secondary products. In addition, 10 to 15% of the glutamic acid used is recovered in solution in the heat-carrier fluid in the form of pyroglutamic acid. Accordingly, the ε-(γ-glutamyl)-lysine is isolated by initially separating the n-amyl alcohol from the conversion product, for example by filtration. The conversion product is then taken up in water, after which the remaining n-amyl alcohol is eliminated by azeotropic distillation with water. The ε-γ-glutamyl)-lysine is then crystallised by cooling and adding methanol. The mother liquors are recovered for recycling lysine and glutamic acid as well as the n-amyl alcohol and the methanol.

The process according to the invention is applicable solely to the production of ε-(γ-glutamyl)-lysine, and cannot be extended to the production of compounds consisting of a basic amino acid other than lysine (ornithine, arginine) and an acidic amino acid other than glutamic acid, for example N-acetyl glutamic acid, aspartic acid and pyroglutamic acid.

The reason for this is that some salts are not formed at all or are not formed in the crystalline phase, for example lysine N-acetyl glutamate, ornithine or arginine pyroglutamate.

Other salts have too low a melting point, such as lysine pryoglutamate which melts at 120° C.

Finally, other salts do not give rise to the required conversion, as shown in the following Table:

| Type of salt | Treatment | Result |
| --- | --- | --- |
| lysine aspartate | 8 h/150° C | no conversion |
|  | 4 h/200° C | decomposition products |
| ornithine glutamate | 8 h/140° C | no conversion |
|  | 3 h/170° C | decomposition products |
| arginine glutamate | 3 h/160° C | decomposition products |

The process according to the invention is illustrated by the following Example. In the light of the intended use of the ε-(γ-glutamyl)-lysine obtained for food purposes, the amino acids used in this Example are natural amino acids of L-configuration. Naturally what is described applies equally to amino acids of D-configuration and the properties of the derivative obtained are the same except for rotatory power.

EXAMPLE

Preparation of L-lysine L-glutamate 187 g of monosodium L-glutamate monohydrate and 182 g of L-lysine hydrochloride are dissolved in 0.4 liter of water at ambient temperature, after which 1.4 liters of methanol are slowly added to the solution obtained. After seeding with a few crystals of L-lysine L-glutamate. $2H_2O$, α-phase, 0.6 liter of methanol are added with vigorous stirring, after which stirring is continued from about 1 hour. The suspension obtained is then centrifuged, giving approximately 3 liters of mother liquors, from which the methanol is recovered, and 365 g of L-lysine L-glutamate dihydrate containing approximately 1% of NaCl.

After centrifuging, this salt is taken up in 0.8 liter of water, followed by the rapid addition to the solutions obtained of 3 liters of methanol. After seeding with a few crystals of L-lysine L-glutamate. $2H_2O$, α-phase, the seeded solution is cooled to 0° C with vigorous stirring. After about 4 hours, the suspension obtained is centrifuged, giving on the one hand approximately 4 liters of mother liquors, from which the methanol is recovered, and on the other hand, after centrifuging and drying, 350 g of L-lysine L-glutamate dihydrate, α-phase. The yield amounts to approximately 90%.

Conversion into ε-(γ-glutamyl)-L-lysine

The 350 g of the L-lysine L-glutamate dihydrate, α-phase, previously prepared, still containing approximately 15% by weight of methanol, are suspended in 0.85 liter of n-amyl alcohol in a nitrogen atmosphere. The n-amyl alcohol is then heated, followed by the distillation at around 70° first of a ternary mixture containing n-amyl alcohol, methanol and water (approximately 0.1 liter) and then of a binary mixture of n-amyl alcohol and water (approximately 0.1 liter). Heating is terminated at the reflux temperature of the n-amyl alcohol i.e. at 138° C. After a total heating time of 20 hours, the precipitate formed is separated by filtration. This gives 400 g of crude product containing ε-(γ-L-glutamyl)-L-lysine and approximately 1 liter of amylic mother liquors from which 20 g of L-pyroglutamic acid are recovered from recycling after conversion into L-glutamic acid. The n-amyl alcohol is purified for recycling.

Isolation of the ε-(γ-L-glutamyl)-L-lysine

The 400 g of the crude product obtained as described above are suspended in 1.2 liters of water, after which the residual n-amyl alcohol is elminated by distillation under reduce pressure at a temperature in the range from 70° to 80° C. 0.2 liter of a mixture of water and n-amyl alcohol is thus recovered, the n-amyl alcohol being purified and recycled. 0.8 liter of methanol are then added to the suspension, followed by cooling while stirring to a temperature of 20° C. After stirring for 1 hour, the crystals obtained are separated. The mother liquors are separated from the methanol which they contain and which is recycled and, after neutralisation to pH-7 with L-glutamic acid, are used instead of water for recrystallisation of the L-lysine L-glutamate. The crystals obtained are washed with 50 ml of methanol and then dried, giving 100 g of ε-(γ-L-glutamyl)-L-lysine, i.e. a total yield of 36%, including preparation of the salt. The purity, as evaluated by thin-layer chromatography and electrophoresis, amounts to between 98 and 99%.

Mp = 245° – 250° C with decomposition
$[\alpha]_d^{25}$ = +6.5° C=2; $H_2O$)

Mp, IR and NMR spectra are identical with those of a reference sample.

We claim:

1. A process for the preparation of ε-(γ-glutamyl)-lysine which comprises heating lysine glutamate for at least 5 hours at a temperature of at least 120° C in a heat-carrier fluid which is (a) immiscible with lysine glutamate, (b) chemically inert to lysine glutamate and (c) possesses a boiling point above 120° C., and isolating ε-(γ-glutamyl)-lysine from the conversion product thus obtained.

2. A process as claimed in claim 1 for the preparation ε-(γ-L-glutamyl)-L-lysine from L-lysine L-glutamate.

3. A process as claimed in claim 1, wherein lysine glutamate dihydrate, α-phase, or lysine glutamate dihydrate, β-phase, is used as starting material.

4. A process as claimed in claim 1, wherein the inert heat-carrier fluid is kerosene, nonane, 1,1,2,2-tetrachloroethane, 1-octanol or 2-ethyl-1-butanol.

5. A process as claimed in claim 1, wherein the inert heat-carrier fluid is n-amyl alcohol.

6. A process as claimed in claim 1, wherein heating is carried out at a temperature in the range from 135° to 150° C.

7. A process as claimed in claim 1, wherein heating is carried out over a period of from 16 to 48 hours.

8. A process as claimed in claim 1, wherein $\epsilon$-($\gamma$-glutamyl)-lysine is isolated by separating it by filtering a suspension of the conversion product in a mixture of methanol and water.

9. A process for the preparation of $\epsilon$-($\gamma$-glutamyl)-lysine which comprises heating lysine glutamate for at least 5 hours in air or nitrogen at a temperature which does not exceed a level at which appreciable decomposition of lysine will occur, and isolating $\epsilon$-($\gamma$-glutamyl)-lysine from the conversion product thus obtained.

* * * * *